United States Patent [19]
Shiber

[11] Patent Number: 6,143,009
[45] Date of Patent: Nov. 7, 2000

[54] FLEXIBLE-AGITATOR SYSTEM AND METHOD

[76] Inventor: Samuel Shiber, 365 Kearney Cir., Manchester, N.H. 03104

[21] Appl. No.: 09/389,712

[22] Filed: Sep. 3, 1999

Related U.S. Application Data

[63] Continuation-in-part of application No. 09/241,802, Feb. 2, 1999, abandoned.

[51] Int. Cl.[7] .................................................. A61B 17/32
[52] U.S. Cl. ............................................................ 606/159
[58] Field of Search .................................. 606/159, 170, 606/167, 180; 604/22

[56] References Cited

U.S. PATENT DOCUMENTS

| | | | |
|---|---|---|---|
| 5,318,576 | 6/1994 | Plassche, Jr. et al. | 606/159 |
| 5,779,721 | 7/1998 | Nash | 606/159 |

Primary Examiner—Michael Buiz
Assistant Examiner—Kevin Truong
Attorney, Agent, or Firm—Samuel Shiber

[57] ABSTRACT

A rotary flexible-agitator system for removing an obstruction from within a patient's vessel that is comprised of a tubular-housing with suction connected to its proximal end, and a motor-driven, rotary, flexible agitator-shaft with an offset distal-agitator disposed in the housing and the offset distal-agitator extending out of the open distal end of the housing. The offset distal-agitator is adapted to break the obstruction in the vessel to pieces while the suction draws the pieces into the housing, where the relative motion between the flexible-agitator and the housing reduces the longitudinal frictional forces between the pieces, the rotary flexible agitator-shaft and the tubular-housing, and where the relative motion between the rotary flexible agitator-shaft and the tubular-housing further breaks the pieces as they pass through the tubular-housing.

15 Claims, 3 Drawing Sheets

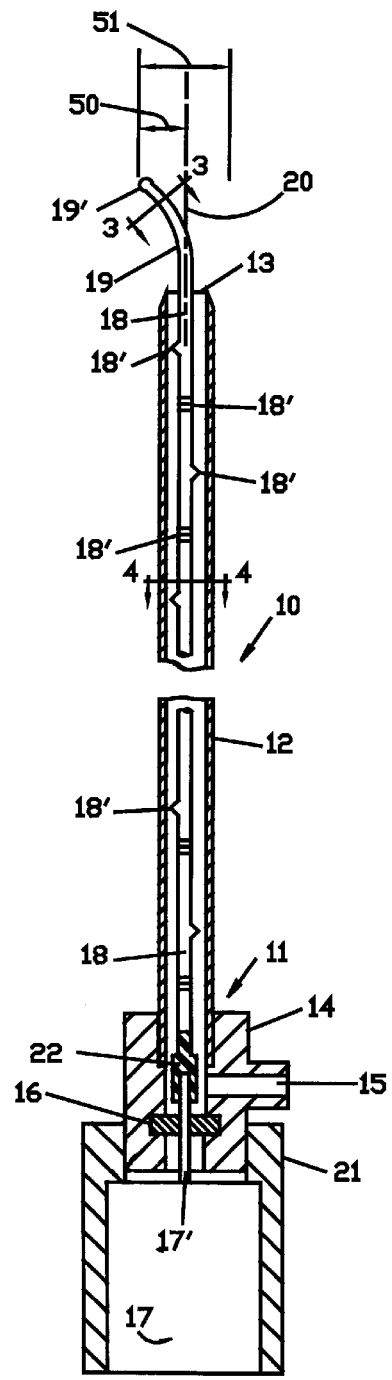
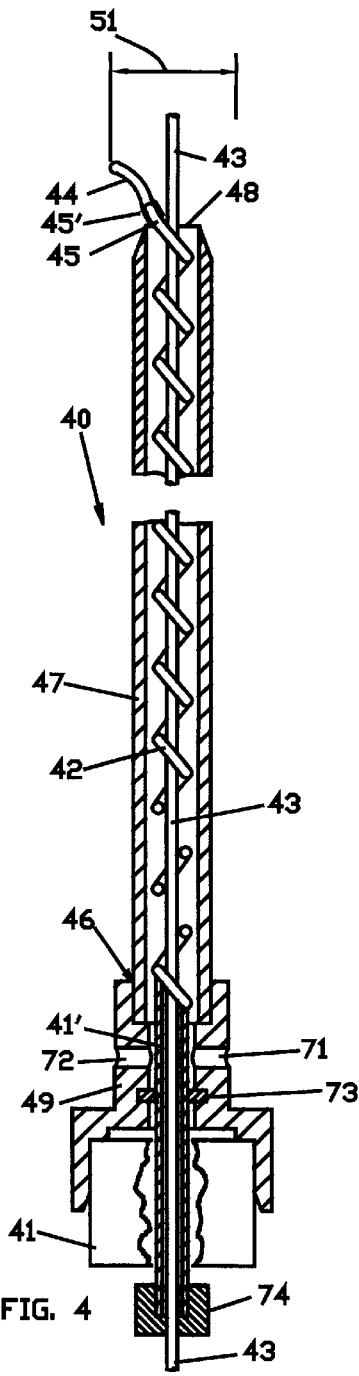
FIG. 1
FIG. 1A
FIG. 1B
FIG. 4

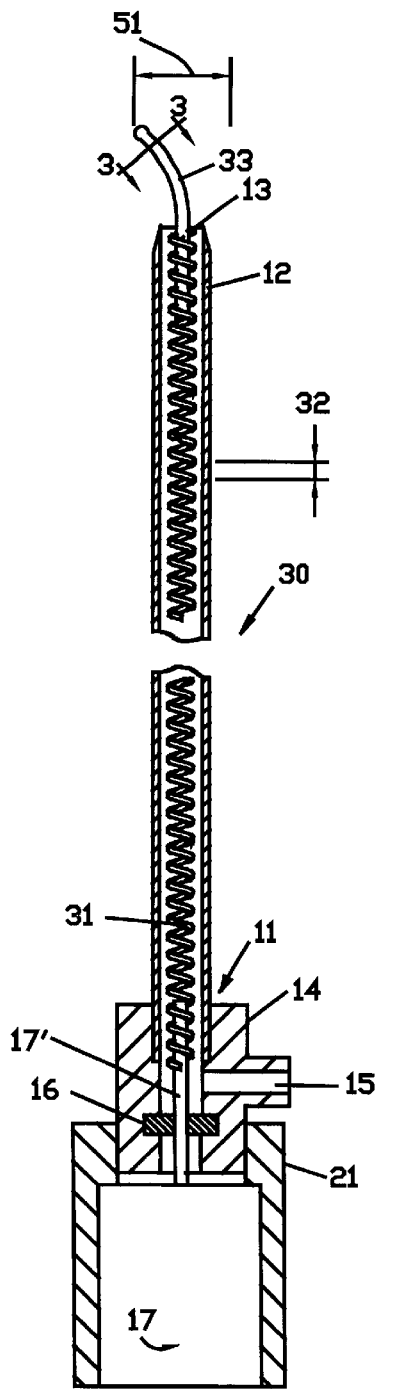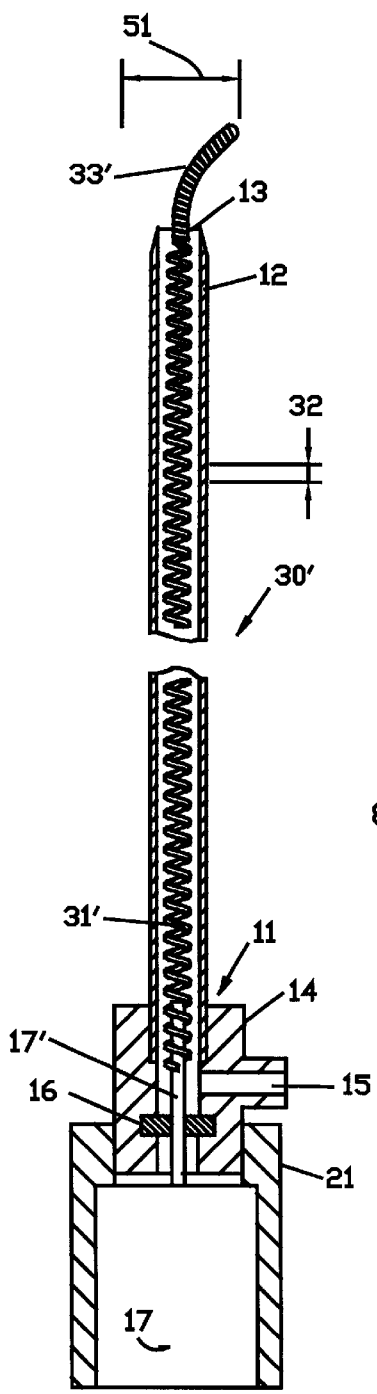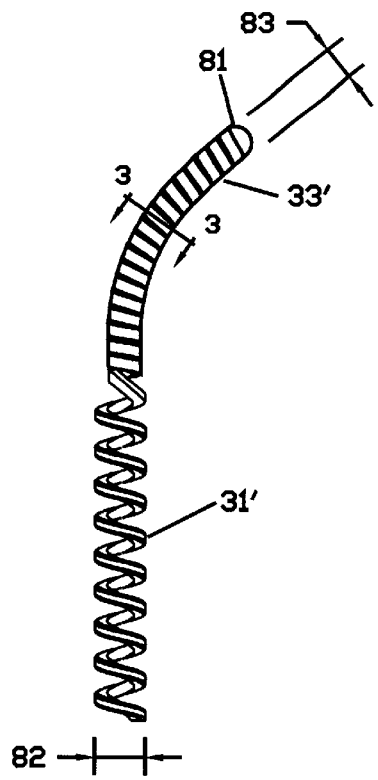
FIG. 3
FIG. 3A
FIG. 3B

FLEXIBLE-AGITATOR SYSTEM AND METHOD

CROSS REFERENCE TO OTHER APPLICATIONS

This application is a Continuation In Part of my application Ser. No. 09/241,802 filed Feb. 2, 1999 now abandoned that is herein being incorporated by reference.

BACKGROUND AND SUMMARY OF THE INVENTION

The rotary flexible-agitator system is designed for removing an obstruction from within a patient's vessel through a relatively small diameter tube and particularly for opening vessels, such as dialysis access grafts, that tend to become obstructed by thrombus.

Current treatments such as pharmacological, surgical or trans-catheter procedures can be time consuming, traumatic and expensive. Thus objects of the present invention are to simplify, improve and shorten the process by breaking the obstruction lodged in the vessel to pieces, and simultaneously extracting the pieces is out of the vessel. These and other objects of the invention will become apparent from the following discussion and the accompanying drawings.

BRIEF DESCRIPTION OF THE FIGURES

FIG. 1 shows a cross-sectional view of a first embodiment of a rotary flexible-agitator system (the midsection of this embodiment and the midsections of the other embodiments are omitted to better fit on the drawing sheet.)

FIG. 1A shows a cross-sectional view of a distal-agitator as viewed on the plane 4—4 marked on FIG. 1.

FIG. 1B shows a cross-sectional view of a first embodiment as viewed on the plane 3—3 marked on FIG. 1.

FIG. 3 shows a cross-sectional view of a second embodiment of a rotary flexible-agitator system.

FIG. 3A shows a cross-sectional view of a third embodiment of a rotary flexible-agitator system that utilizes an agitator-shaft and a distal-agitator that are made from a continuous flat wire.

FIG. 3B shows an enlarged view of the distal portion of the agitator-shaft and the distal-agitator used in the third embodiment. The agitator-shaft is produced from the flat wire wound on its edge and the distal-agitator is produced from the continuation of the flat wire twisted one-quarter of a turn and wound on its flat side.

FIG. 4 shows a cross-sectional view of a fourth embodiment of a rotary flexible-agitator system designed to operate over a guidewire.

DETAILED DESCRIPTION OF THE DRAWINGS

Figure 2:
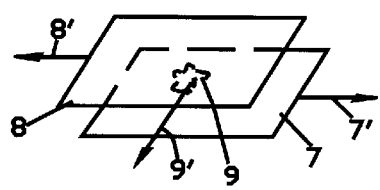
FIG. 2 shows a perspective view of a flat model that is used to explain how the relative motion between a rotary flexible agitator-shaft and a flexible-tube enables the suction to move obstruction pieces through the flexible-tube.

FIG. 1 shows a rotary flexible-agitator system 10 for removing an obstruction (e.g., thrombus) from within a patient's vessel. The system is comprised of a tubular-housing 11 (similar parts shall be denoted by the same numerals throughout the FIGURES) made of a flexible-tube 12 with an open distal end 13 ("distal end" referring to the end that goes further into the vessel and "proximal end" referring to the other end) and a proximal end 14. The proximal end of the tubular-housing defines a suction port 15 that is connected to the proximal end of the flexible-tube 12. A seal 16 is seated in the proximal end of the tubular-housing.

A motor 17 (e.g., an electric motor, an air-driven turbine or other suitable drive) is conventionally connectable to an appropriate power source (e.g., a battery or a compressed air supply, respectively, or other suitable power source.) The connection and the power source are not shown. The motor has an output shaft 17' that fits in and is coupled to a hollow proximal end 22 of a flexible rotary agitator 18.

The rotary flexible agitator-shaft is disposed in the tubular-housing and is preferably made from plastic in one piece with a curved flexible offset distal-agitator 19 that extends out of the open distal end 13 of the tubular-housing. The curved shape of the offset distal-agitator offsets its rounded end 19' away from the axis 20 of the tube 12 by a distance 50. The cross section of the offset distal-agitator (viewable on plane 3—3 marked on FIGS. 1, 3 and 3B), that is illustrated in FIG. 1B, is sufficiently small and the offset distal-agitator is sufficiently flexible to be inserted through the tube 12.

While the offset distal-agitator rotates, its effective diameter 51 (i.e., the diameter within which it engages the obstruction material) is substantially larger than the opening through the tube 12 through which the agitator-shaft and the offset distal-agitator are inserted. Therefore, the size of the entry wound that is required for insertion of the system into the vessel (note FIGS. 5 and 6) and the associated trauma to the vessel is reduced.

A sleeve 21 fits over and aligns the motor 17 with the proximal end 14 and the flexible-tube 12.

As the offset distal-agitator breaks the obstruction in the vessel, the pieces are drawn into the open distal end 13 by suction applied to the proximal end of the flexible-tube 12 through the port 15. As the pieces enter the flexible-tube 12, the relative rotational motion between the rotary flexible agitator-shaft and the flexible-tube reduces the longitudinal friction that can inhibit the motion of the pieces in the flexible-tube 12, as explained hereinafter in connection with FIG. 2, and assists the suction in moving the obstruction pieces through the flexible-tube 12. As the obstruction pieces move through the flexible-tube 12, the relative rotational motion tends to further breakdown the pieces with protrusions 18', making it easier for the suction to move them through the tubular-housing 11.

FIG. 2 shows a perspective view of a flat model that is used to explain how the relative rotational motion between the agitator-shaft and the tube reduces the resistance to the movement of obstruction pieces through the tube.

The model is comprised of a first plane 7 moving in a direction denoted by an arrow 7', a second plane 8 moving in an opposite direction denoted by an arrow 8' and a piece of obstruction 9 that is sandwiched between the planes. Due to these motions full frictional forces develop between the piece 9 and the planes in a direction parallel to the arrows 7' and 8'. If at the same time, even a small additional force is exerted on the piece 9 in a direction 9' (that is perpendicular to arrows 7' and 8') it will change the direction of the overall resultant force acting on the piece and cause movement in the direction 9'. Absent the above mentioned relative movement between the planes 7 and 8, the force that would have to be exerted on the piece 9 in the direction of arrow 9' would have to be larger than the full frictional force that can develop between the piece 9 and both planes 7 and 8. If plane 7 is envisioned as the outside surface of the agitator 18 and plane 8 is envisioned as the inside surface of the tube 12 and the small force in the 9 direction is envisioned to be the force that suction exerts on the obstruction pieces, it can be understood how the relative rotational motion between the flexible-agitator 18 and the flexible-tube 12 assists the suction applied to port 15 to longitudinally move the obstruction pieces through the flexible-tube 12.

FIG. 3 shows a cross-sectional view of a second embodiment of a rotary flexible-agitator system 30 wherein the rotary flexible-agitator is comprised of a spiral 31, preferably made of metal (e.g. stainless steel, Nitinol or other bio-compatible alloy) wire, that is disposed in the tubular-housing 11. A few of the spiral's proximal coils closely fit over the shaft 17' and are coupled to it. A few of the spiral's distal coils closely fit over an offset distal-agitator 33, that is preferably made of plastic, and are coupled to it. As in the other embodiment, the effective diameter of the offset distal-agitator is indicated by numeral 51, and it is substantially larger than the opening of the tube 12 through which both the spiral 31 and the offset distal-agitator 33 have to be inserted (note plane 3—3 that is marked on both FIG. 3 and on FIG. 3B on which the cross section of the offset distal-agitator is defined).

Figure 6:
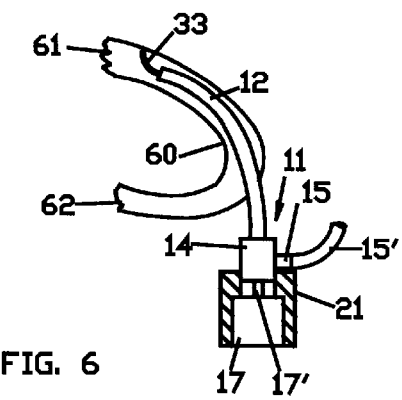
FIG. 6 shows the items of FIG. 5 where a flexible offset distal-agitator is connected through a flexible agitator-shaft (hidden inside the tubular-housing) to a motor and is inserted into the tubular-housing to form a rotary flexible-agitator system.
Figure 7:
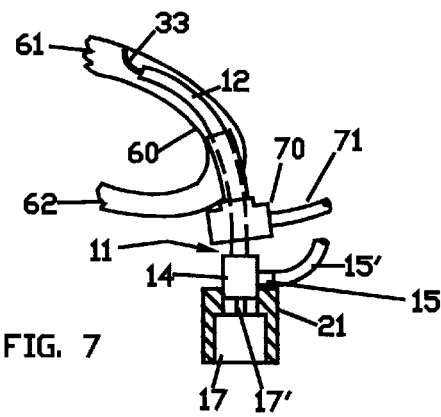
FIG. 7 shows a rotary flexible-agitator system, inserted in a hemodialysis access graft through a short introducer, with its own sidearm, through which fluid can be introduced into the graft.

In addition to agitating the obstruction pieces inside the flexible-tube 12, the midsection of the spiral acts as a flexible shaft for transmitting rotation and torque from the motor 17 to the distal-agitator 33. Preferably, the spiral is core-less (i.e., the torque is carried by the spiral the and there is either no central member or such member has no substantial power transmitting function) and the linear length of the wire that is used to form the spiral 31 is substantially greater than that of a conventional, non-spiraled, shaft. This increased length of wire increases the flexibility of the agitator-shaft (i.e., it reduces the stresses that develop in the wire, and it reduces the side force that develops between the agitator-shaft, the flexible-tube and graft) which is advantageous when the a rotary flexible-agitator system is operated in a curved vessel as, for example, is illustrated in FIGS. 6 and 7.

FIG. 3A shows a cross-sectional view of a third embodiment of a rotary flexible-agitator system 30', wherein the agitator-shaft 31' and the offset distal-agitator 33' are made from one continuous flattened spiral wire (the narrower side of the flattened wire's cross-section will be referred to as an "edge" and the wider side as a "flat side".) The portion of the wire that makes up the agitator-shaft is wound on its edge as illustrated in FIG. 3B. This further increases the flexibility and torque is carrying capacity of the agitator-shaft (as compared to a spiral wound of a wire with a round cross section). The portion of the wire that makes up the distal-agitator is wound on its flat side as also illustrated in FIG. 3B. This reduces the gap between the coils and the likelihood of material being caught between them and it also lends itself to the manufacturing of the agitator-shaft with an overall cross-section (the diameter of which is denoted as 82) that is larger than the overall cross-section of the offset distal-agitator (the diameter of which is denoted as 83) which in turn leaves more of the distal end 13 open for the pieces to enter the flexible-tube 12. The distal end 81 of the offset distal agitator is rounded to decrease the likelihood of damaging the vessel.

The motors shaft 17' is preferably rotated in a direction so that the relative motion between the spiral wire and the flexible-tube 12 assists the suction applied at port 15 in conveying the obstruction material into the open distal end 13 and through the flexible-tube 12. However, since the flow through the tube is not synchronized with advancement of the spiral (which is the product of the spiral's rotational speed multiplied by the spiral's pitch 32), the relative motion between the rotating spiral and the flexible-tube 12 further breaks the pieces as they pass through the flexible-tube 12.

When the motor's direction of rotation is reversed the mechanical pumping action of the spiral is also reversed and works against the suction in conveying the obstruction material through the flexible-tube 12. However, by increasing the spacing between the spiral and the wall of the flexible-tube 12, or by changing the pitch 32 of the spiral, the mechanical pumping action of the spiral can be adjusted so that the suction applied at the port 15 will dominate the direction of the flow through the flexible-tube 12. While the reversal of the mechanical pumping action reduces the rate of flow through the flexible-tube 12, it increases the opportunity of the obstruction pieces to collide with the rotating spiral and be broken down more. Optionally, the motor can be periodically, manually or automatically, reversed to assist in releasing pieces of the obstruction that may have become stuck in the flexible-tube 12 or wrapped around the agitator. (This technique is applicable to any of the embodiments.)

FIG. 4 shows a cross-sectional view of a fourth embodiment of a rotary flexible-agitator system 40. In this embodiment the shaft 41' of the motor 41 is a tube, that together with a spiral 42, which is affixed and coupled to its distal end, define a continuous passageway that can accommodate a guidewire 43 or similar elongated object (e.g., an optic fiber or an ultrasound probe). The spiral 42 is also preferably made of a metal wire and its distal end 45 is affixed to a hollow end 45' of an offset distal-agitator 44.

The fourth embodiment's tubular-housing 46 is comprised of a flexible-tube 47 with an open distal end 48 and a proximal end 49 which defines a suction port 71, that is connected to the proximal end of the flexible-tube 47. An optional second port 72 can be used to introduce fluid into the proximal end 49. Such fluid can be used to dilute the slurry of obstruction pieces that are suctioned through port 71. A seal 73, seated in the proximal end of the tubular-housing, minimizes leakage around the motor shaft. A seal 74, that is attached to the proximal end of the shaft 41', minimizes leakage around the guidewire 43 and through the shaft 41'. The proximal end 49 defines an open cylinder that fits around the motor 41 and concentrically aligns the motor with the flexible-tube 47.

Figure 5:
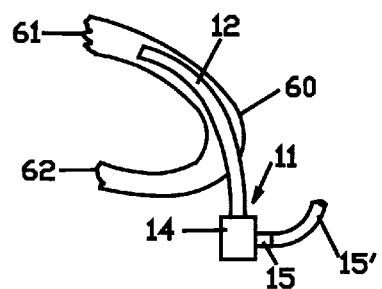
FIG. 5 shows a tubular-housing inserted in a "U" shaped hemodialysis access graft (shown with its ends severed.)

FIG. 5 shows the tubular-housing 11 inserted in a vessel such as a "U" shaped hemodialysis access graft 60 (the graft's ends, 61 and 62, are normally connected to a vein and an artery. The vein and the artery are not shown).

FIG. 6 shows a rotary flexible-agitator system where a flexible offset distal-agitator 33 is connected to a flexible agitator-shaft that is disposed (and hidden) in the tubular-housing 11 and is connected to a motor's shaft 17'.

FIG. 7 shows the rotary flexible-agitator system, inserted in a the hemodialysis access graft 60 through a commercially available introducer 70 with its own side arm 71, through which fluid can be introduced into the graft.

The process of removing an obstruction from the vessel 60 can be comprised of the following steps:

Inserting a tubular-housing 11 into the vessel 60 as shown in FIG. 5. Tubular-housing 11 can be a commercially available introducer sheath of the type that is commonly used to gain percutaneous access to a patient's vessels or a similar structure. When such an introducer is inserted into a vessel it is usually inserted over a closely fitting dilator, which is retracted once the introducer is in the vessel, leaving the seal 16 (note FIG. 1) to seal the proximal end of the introducer. At this point, which is illustrated in FIG. 5 suction can be applied to the port 15 through a tube 15', to try and remove the obstruction. Alteratively or adjunctively, if suction alone does not sufficiently remove the obstruction, the motor driven rotary flexible-agitator, with the offset distal-agitator, can be inserted through the seal 16 until the offset distal-agitator extends out of the open distal end of the tubular-housing and the motor 17 is seated in the sleeve 21 that concentrically aligns it with the tubular-housing as illustrated in FIG. 6.

Then suction can be applied and the motor activated to rotate the rotary flexible agitator-shaft and the offset distal-agitator. As the offset distal-agitator breaks the obstruction (not shown) in the vessel 60, the suction draws the pieces through the open distal end into the flexible-tube 12.

The relative motion between the rotary flexible agitator-shaft and the tubular-housing 11 reduces the longitudinal frictional forces (frictional forces that oppose the advancement of obstruction pieces through the flexible-tube 12), allowing the pieces to be suctioned through the tube. In addition, the relative motion between the flexible-tube 12 and the radial protrusions 18' of the rotary flexible agitator-shaft shown in FIG. 1 or of the spiral windings shown in FIG. 3 further break the pieces as they pass through the tubular-housing 11.

When the fourth embodiment that is shown in FIG. 4 is used, a preparatory step of inserting a guide wire (as previously mentioned, similarly shaped elongated items such as optical fibers or ultrasonic transducers can also serve as guidewires) is added. Then the embodiment of FIG. 4 can be inserted and directed over the guidewire to break down the obstruction and suction it through the tubular-housing 46 similarly to the other embodiments.

The rotary flexible-agitator system can be inserted directly into the obstructed vessel, as shown in FIG. 6, or it can be inserted through an introducer, as shown in FIG. 7. The introducer is preferably equipped with a side arm through which fluid (e.g., saline solution containing heparin and radio-opaque contrast material) can be introduced into the vessel (to prevent reoccurrence of thrombi and assist in fluoroscopically imaging the process, respectively).

It should be understood that the number and sequence of steps can be modified within the scope of the claims and that modifications and substitutions may be made to the embodiments that have been used to illustrate the invention without departing from the spirit of the invention or the scope of the claims.

I claim:

1. A rotary flexible agitator system for removing an obstruction from within a patient's vessel comprising in combination:

a tubular housing having a flexible tube with an open distal end and a proximal end section with a suction port, a motor driven rotary flexible agitator-shaft disposed in the tubular housing, said agitator having an offset distal agitator attached to its distal end that extends out of the open distal end, the effective diameter of the offset distal agitator being substantially larger than its cross section, wherein the rotating offset distal agitator is adapted to break the obstruction in the vessel to pieces and the relative motion between the rotary flexible agitator and the flexible tube reduces the longitudinal friction that may resist the movement of the pieces through the flexible tube.

2. As in claim 1 wherein the agitator-shaft comprises a spiral wire.

3. As in claim 2 wherein the agitator-shaft and the offset distal-agitator are made from one continuous wire.

4. As in claim 3 wherein the agitator-shaft is made of a flattened wire wound on its edge and the distal-agitator is made from the flattened wire wound on its side.

5. As in claim 3 wherein the cross-section of the agitator-shaft is larger than the cross-section of the offset distal-agitator.

6. As in claim 3 wherein the a distal end of the agitator shaft is coupled to the flexible offset distal-agitator that is made of a plastic material.

7. As in claim 2 wherein the spiral wire is core-less.

8. As in claim 1 wherein a distal end of the agitator-shaft is coupled to a flexible offset distal-agitator that is made of a plastic material.

9. As in claim 1 wherein the distal end of the flexible-tube is curved.

10. As in claim 1 wherein the rotary flexible agitator-shaft has radial protrusions that, during the relative motion between the rotary flexible agitator-shaft and the flexible-tube, further break the pieces as they pass through the flexible-tube.

11. A process of removing an obstruction from a vessel comprising the following steps:

inserting a rotary flexible-agitator system, having a flexible tubular-housing containing a motor driven rotary flexible agitator-shaft with an offset distal-agitator, which extends out of a open distal end of the flexible tubular-housing, into a patient's obstructed vessel, the effective diameter of the offset distal agitator being substantially larger than its cross section, causing the motor to rotate the rotary flexible agitator-shaft and the offset distal-agitator so that the offset distal-agitator breaks down the obstruction in the vessel while suction draws the broken pieces into the tubular-housing, where the relative motion between the rotary flexible agitator-shaft and the tubular-housing reduces the longitudinal frictional forces thereby enabling the suction of the pieces through the tubular-housing.

12. As in claim 11 wherein the relative motion between the rotary flexible agitator-shaft and the tubular-housing further breaks down the obstruction pieces as they pass through the tubular-housing.

13. As in claim 11 wherein the rotary flexible-agitator system is inserted into the vessel through an introducer.

14. As in claim 13 wherein the introducer has a side arm through which fluid is introduced into the vessel.

15. As in claim 14 wherein the fluid is a saline solution containing heparin and radio-opaque contrast material to facilitate fluoroscopic imaging.

* * * * *